United States Patent [19]
Parker et al.

[11] Patent Number: 5,548,120
[45] Date of Patent: Aug. 20, 1996

[54] LINEAR INTEGRATING CAVITY LIGHT SOURCE FOR INFRA-RED ILLUMINATION OF SENSITIZED MEDIA

[75] Inventors: H. Galen Parker, Rochester; Robert B. Bilhorn, Webster; Martin C. Kaplan; Russell J. Palum, both of Rochester, all of N.Y.

[73] Assignee: Eastman Kodak Company, Rochester, N.Y.

[21] Appl. No.: 339,052

[22] Filed: Nov. 14, 1994

[51] Int. Cl.$^6$ .................................. F21V 7/00; F21V 7/04
[52] U.S. Cl. ................... 250/341.7; 250/228; 250/494.1; 250/495.1; 250/359.1; 356/236
[58] Field of Search .................................. 250/341.7, 228, 250/359.1, 494.1, 495.1; 356/236

[56] References Cited

U.S. PATENT DOCUMENTS

| | | |
|---|---|---|
| 4,639,608 | 1/1987 | Kuroda . |
| 4,814,667 | 3/1989 | Tanaka . |
| 4,868,383 | 9/1989 | Kurtz et al. . |
| 4,899,040 | 2/1990 | Davis et al. . |
| 4,933,779 | 6/1990 | Milch . |
| 4,954,914 | 9/1990 | Karita et al. . |
| 5,019,710 | 5/1991 | Wennerberg et al. ............... 250/341.7 |
| 5,144,117 | 9/1992 | Hasegawa et al. . |
| 5,150,016 | 9/1992 | Sawase et al. . |
| 5,241,459 | 8/1993 | Kaplan et al. ...................... 250/228 X |
| 5,274,228 | 12/1993 | Kaplan ................................ 250/228 X |

FOREIGN PATENT DOCUMENTS

62-275247   5/1989   Japan .

*Primary Examiner*—Carolyn E. Fields
*Assistant Examiner*—Edward J. Glick
*Attorney, Agent, or Firm*—Clyde E. Bailey, Sr.

[57] ABSTRACT

A highly uniform infrared illumination source for illuminating a stripe of a moving sensitized web for line scan imaging of imperfections in the coating on the web by a CCD imaging camera. A light integrator having an elongated housing formed with side and end walls defines a linear light integrating cavity having diffusely reflecting interior wall surfaces. An elongated array of infrared LEDs is spaced along the side wall for emitting light into the cavity for integration within the cavity. A longitudinally extending slit is formed in the side wall through which a diffuse, linear light beam exits the elongated slit having a varying longitudinal intensity profile. The intensity of the light emitted by the LEDs is modulated in an intensity pattern that alters the varying longitudinal intensity profile of the linear light beam to provide a desired longitudinal intensity profile of the stripe of diffuse illumination. Preferably, the intensity modulation renders more uniform the longitudinal intensity profile of the linear light beam illuminating the web as viewed by the imaging camera. The desired light intensity profile along the length of the emitted light beam is achieved by clustering the LEDs with LED drive circuits operated at different drive currents as a function of a set point control signal appropriate to the characteristics of the imaging camera and a transmitted light intensity feedback signal to maintain the intensity pattern of the LEDs and the uniform intensity profile as viewed by the imaging camera regardless of the optical density of the web.

23 Claims, 7 Drawing Sheets

LINEAR INTEGRATING CAVITY LIGHT SOURCE FOR INFRA-RED ILLUMINATION OF SENSITIZED MEDIA

Cross Reference to Related Applications

Cross-reference is hereby made to commonly assigned, co-pending U.S. Pat. application Ser. No. 07/891,318, filed May 29, 1992, and entitled Coating Density Analyzer and Method using Image Processing and Ser. No. 08/263,639 filed Jun. 22, 1994, and entitled Light Pipe Spectral Filter.

FIELD OF THE INVENTION

The invention relates in general to the detection of coating imperfections on a coated web, particularly a sensitized photographic film, and more particularly to a linear integrating cavity light source for providing a line of uniform intensity infra-red light to illuminate a moving web for detecting coating imperfections therein.

DESCRIPTION OF THE BACKGROUND ART

Research and development efforts in the photographic materials and paper materials industries often focus on detecting various types of imperfections in a moving coated web, e.g. a sensitized film or paper web. These imperfections may, for example, result from disturbances in process of coating the film base or paper with sensitized layers. Research and development efforts attempt to isolate, through process modeling, the source of an on-going disturbance-type in a coating process once the imperfections are identified. In addition, in the commercial production of such sensitized media, the detection and location of imperfections in wide and long webs is conducted so that the imperfections may be avoided when the webs are severed into film and paper strips for packaging in light tight containers. Moreover, on-line web imaging may be used for process control applications.

Coating imperfections of particular interest are continuous-type imperfections or streaks and point-type or two-dimensional imperfections. These imperfection types, which can occur in one or more coating layers on a support web, are typically indicative of a disturbance or design related problem in the coating process.

An effective on-line imperfection recognition system and method would enable one to discern, characterize and confirm various models of the coating process, thereby determining the disturbance causing such an imperfection. Two significant issues, however, must be addressed by any imperfection recognition system before adequate optical data can be collected from sensitized coatings under examination. First, the system must be able to extract small density changes from the obtainable spatial and temporal noise background. Secondly, the system must provide adequate, uniform illumination within the spectral bandwidth of the usable contrast range, while avoiding fogging of any sensitized coating layers.

State-of-the-art efforts to quantify moving web disturbances have most commonly been implemented as laser scanning systems. For example, continuous laser beams are often swept by multifaceted polygon mirror scanners across moving webs of sensitized film or paper, and focused with dedicated optics onto a discrete detector such as a photomultiplier tube. Various detector configurations enable data acquisition in either a reflective or transmissive mode. Unfortunately, such laser scanner packages can be expensive and typically have limited anomaly detection capabilities.

Specifically, such laser scanning packages are almost universally unable to process data associated with very narrow lines and streaks which may be embedded in noise. (Also, laser scan output processing packages, in general, remain less sophisticated than those accompanying state-of-the-art imaging technologies such as solid state cameras.) Therefore, a need is recognized to exist today in the photographic and paper materials industry for a more effective and less expensive technique to extract and characterize imperfections from background data including inherent noise variations, and particularly low-level, narrow continuous-type imperfections or streaks in a moving coated web.

A potentially effective means of web coating streak detection may be realized with solid state image sensing technology. Solid state CCD cameras have been described in the above-referenced '318 application in the detection and analysis of a number of coating imperfections. A two-dimensional 512×512 pixel array CCD camera is described for detecting light transmitted through the moving web that is modulated in intensity by the coating layers. Infrared light transmitted through the web is generated by a light integrating sphere that illuminates the array area. Both continuous and strobed illumination may be employed, depending on the mode of detection of streaks or point-type imperfections.

Linear light integrators are well known light sources in the art of image scanning and digitizing, where an image is fixed on a media, e.g. paper sheets, movie film, radiographic film sheets or the like. Linear light integrating cavities are typically used in scanning image frames of developed negative or positive film strips in film image frame digitizing systems of the type described in commonly assigned U.S. Pat. No. 4,868,383 and in the above referenced '639 application. Such linear light sources typically employ an external lamp(s) and lens and filter system which direct a light beam into the integrating cavity through an input port(s). As identified in the above-referenced '383 patent, the lamp(s) can be, for example, xenon or tungsten halogen lamp(s). As described therein, filtration for blocking infra-red wavelengths and emphasizing the blue light to scan negative film is necessary with these lamps.

In the above referenced '639 application, an improved linear light integrator is described employing a light pipe with spectral filtration for filtering the line of light emitted from the integrating cavity. With such filtration of the emitted light, it is possible to locate the light source within the integrating cavity for greater efficiency. Again, the filtration involves elimination of the infra-red light for scanning fully developed film images.

Others have suggested placing discrete lamps in a row within a light integrating cavity, as illustrated in Japanese Patent Application 62-275247, but have noted the problems in intensity variation along the length of the line of light attributed to lamp pitch. In U.S. Pat. No. 4,814,667, a linear light source for a photo copier employing an array of LEDs imaged through a lens is described, wherein the spacing between groups of LEDs is varied to even out the intensity variations encountered with even spacing.

Problems to be Solved by the Invention

In such scanners for use in either inspecting webs for defects or scanning images, a problem remains in achieving a uniform intensity profile in the linear light beam as it is viewed at the imaging camera. Particularly in scanning sensitized media, a problem arises in attaining a uniform intensity profile with low level, infrared illumination that can be used with CCD cameras with an integration function in accurately identifying and discriminating streaks and point-type imperfections in the sensitized coating layers of the media.

SUMMARY OF THE INVENTION

Accordingly it is an object of the present invention to provide a uniform intensity linear light source for illuminating a moving web.

It is a further object of the present invention to provide an efficient light integrator for integrating light from an array of low intensity light sources and for emitting a linear beam of low intensity diffuse light for use particularly in the inspection and analysis of defects in sensitized media that is uniform in intensity when viewed from a camera imaging plane.

These and other objects are realized in a linear light integrator for illuminating a web with an elongated stripe of diffuse illumination comprising: an elongated housing formed with side and end walls defining a light integrating cavity having diffusely reflecting interior wall surfaces, the housing side wall having a longitudinally extending slit through which diffuse light exits the cavity; an elongated array comprising a plurality of discrete light sources supported with respect to the elongated housing to emit light into the cavity, whereby the emitted light is integrated within the cavity by reflection from the interior wall surfaces thereof and the integrated light forms a linear light beam exiting the elongated slit having a varying longitudinal intensity profile; and means for modulating the intensity of the light emitted by the discrete light sources in a predetermined intensity pattern for altering the varying longitudinal intensity profile of the linear light beam to provide a desired longitudinal intensity profile of the stripe of diffuse illumination.

More specifically, the light integrator is employed with infrared LEDs as the light sources to provide a longitudinally uniform intensity profile illuminating a stripe of sensitized photographic film imaged in a line scan by a CCD camera for detection of imperfections in the coated photosensitive layers.

The intensity of the light emitted by the LEDs is modulated in an intensity pattern that compensates and renders more uniform the longitudinal intensity profile of the stripe of light as viewed from the CCD camera. The linear intensity profile along the length of the emitted light beam is achieved by clustering the LEDs into groups with LED drive circuits that energize the groups of LEDs with differing drive currents resulting in differing light intensities of the LEDs in each group. When integrated in the light integrator, the differing intensities provide a compensated linear light intensity profile that compensates for the non-uniformity in the light beam.

The drive circuits are controlled by a set point signal so that the average intensity of the linear light beam emitted from the light integrator exit slit as viewed at the CCD camera is low enough to avoid fogging sensitized film and high enough to efficiently operate the CCD camera. The average light intensity transmitted through the scanned web is detected to provide an intensity feedback signal that is used to control the LED drive circuits to attain the desired average light intensity at the CCD camera.

Advantages of the Invention

Through the use of the inventive light integrator, intensity profile uniformity variation as imaged onto the CCD camera remains within a few percent of the mean. Near-infrared spectral wavelengths may be employed at uniform, low intensities to avoid destructive imaging or fogging of the sensitized media. The intensity feedback ensures constant illumination levels, as viewed by the camera sensor, for a range of coating densities. Remote set point programming overcomes the relative inaccessibility of the camera and light source as installed on a coating machine.

BRIEF DESCRIPTION OF THE DRAWINGS

These and other objects, advantages and features of the present invention will be more readily understood from the following detailed description of the preferred embodiments thereof, when considered in conjunction with the drawings, in which.

DETAILED DESCRIPTION OF THE PREFERRED EMBODIMENTS

As noted initially herein, the present invention is directed to an automated imaging system and method to recognize imperfections in coated web material, such as a photographic film or paper web with one or more sensitized coatings. The invention is described in detail herein in connection with the analysis of a predetermined imperfection-type, such as continuous-type imperfections in a moving, sensitized web. However, those skilled in the art will recognize that the invention is not limited to the specific type of web described, or to whether the web is moving or fixed. Further, various uses/enhancements are readily conceivable by one skilled in the art, all of which are intended to be encompassed by the appended claims.

An imaging system based on detection of reflective light off a moving web material is effective for certain surface coating imperfections. However, in products having multiple coating layers, with the possibility of covered layer imperfections, detection of anomalies using transmissive lighting provides for more efficient image analysis. Therefore, the following discussion centers on detecting streaks in a sensitized web, and an accompanying method, dedicated to a transmissive web illumination approach.

Figure 1:
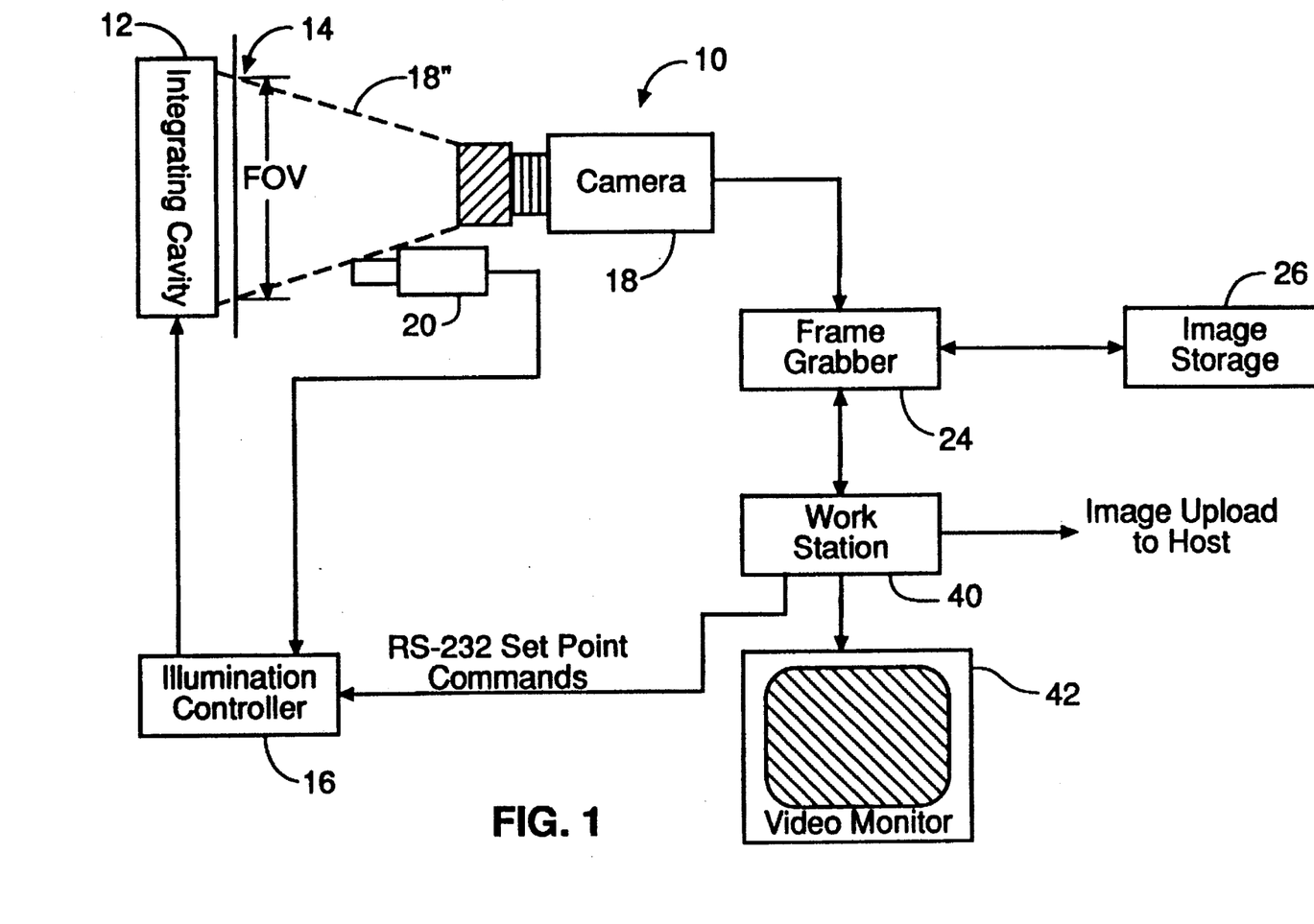
FIG. 1 schematic illustration of the major components of one embodiment a film scanner employing the linear light source pursuant to the present invention.
Figure 2:
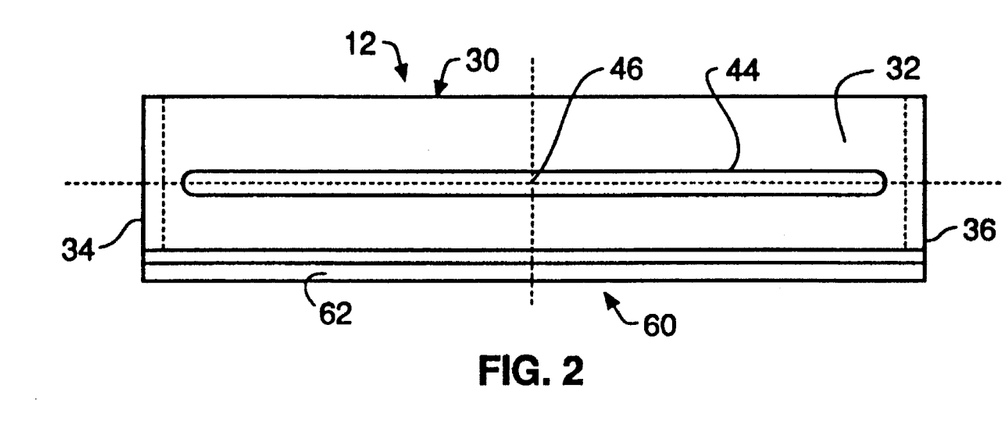
FIG. 2 is a plan view of a linear light intergrator housing for emitting a linear light beam onto the coated web of FIG. 1.
Figure 3:
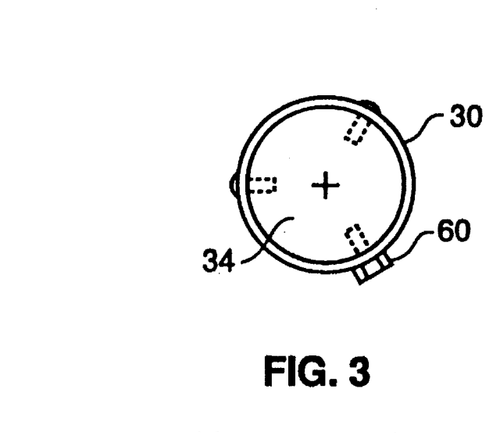
FIG. 3 is an end view of a linear light integrator housing of FIG. 2.

FIG. 1 depicts one embodiment of the film scanner, generally denoted 10, constructed pursuant to the present invention. Scanner 10 includes a linear light source 12 described below in detail which supplies transmissive illumination to a moving, sensitized film web 14 to be scanned and analyzed for imperfections. Light source 12 is operated under the control of illumination controller 16 either as a temporally constant uniform source, or a strobed source, for the capture of discrete web images. As stated above, a strobe light source is preferred for recognition of spot-type imperfections or two-dimensional imperfections in a moving web, while a constant light source is preferred for detection of continuous-type imperfections or streaks.

A linear light beam of infrared radiation is emitted across the width of the coated web 14 and illuminates a stripe of the web 14 of a certain width. For example, the coated width of the web 14 that is illuminated may be about 6 inches (15.2 cm), and the illuminated stripe is about 0.5 inches (1.2 cm) wide in the direction of movement of the web 14. The coated web 14 is transported within close proximity (for example, 1–2 cm) to the exit slit of the light source 12.

A CCD camera 18 and feedback photodetector 20 are mounted in proximity of the web 14 and imaged on the illuminated stripe. The photodetector 20 samples cavity light output after it has radiated through the coated web 14, and provides a feedback signal for the illumination controller 16 in a manner described below for effectively maintaining constant illumination levels for a range of sensitized coating densities.

The CCD camera 18 may take a variety of forms for the line scan of an image of the illuminated stripe of the web. A one-dimensional, 1×2048 pixel CCD camera may be sufficient for use as CCD camera 18. To provide a good signal-to-noise ratio, the camera may utilize a cooled element or may be operated in a chilled environment to minimize thermally induced noise.

Of particular interest in this environment are the expanded gray scale ranges possible with state-of-the-art 10-bit CCD camera technology. A 10-bit system provides a theoretical response range of 1024 gray levels, and after taking noise into consideration, provides a practical usable range on the order of 9 bits.

The pixel image data from the CCD camera 18 are applied as 10-bit digital camera output signals each representing the gray level of each pixel of each imaged line of the moving web 14 to a SUN work station 40 through the operation of a Datacube frame grabber 24. Frame grabber 24 includes a digitizer for digitizing the discrete analog charge packets, corresponding to each pixel, a frame array storage matrix, an 8-bit to 10-bit converter and a display. Regardless of the CCD camera type used, the video camera synchronization is slaved to the frame grabber 24, so that the pixel-to-pixel data corresponds to the frame array storage matrix. A hard disk image storage 26 is coupled to the frame grabber 24 to enable two-dimensional image archiving of the image flames in order to retrieve the frame data for off line signal processing and analysis at a later time if needed.

In this manner, the CCD camera 18 output signal is formatted by means of the frame grabber 24, which sequentially accumulates digitized representations of two-dimensional image frames. Subsequent image data analysis is achieved with software in the work station 40. The digitized image frame signals are applied to the work station 40 which controls operations and retrieves the image data for processing, and an image of the web 14 can be displayed on the monitor 42. The signals may also be uploaded to a host computer and associated external memory, and a printer. The processing of the image frame signals is further described in the above-referenced '318 application and forms no part of the present invention.

The illumination controller 16 controls the illumination intensities of the array of LEDs in the linear light source 12 in response to a set point command signal provided by the work station 40 and a feedback signal from the photodetector 20 to maintain a constant average illumination level at the CCD camera 18 for a range of coating densities. Transmitted density values for a wide range of B&W and color film codes can be expected to vary for the most part from near 0 through 2.0 optical density units. The work station 40 provides the set point command signal in RS-232 code to power LED drive circuits in the illumination controller 16, in a manner described below, at a certain intensity in the absence of a web 14 in the web scanning plane.

In this regard, it is desirable to maintain the illumination intensity of the light stripe falling on the sensitized web 14 low enough to avoid noticeable fogging of the sensitized coatings at the speed of movement of the web. On the other hand, it is also desirable to maintain an 80% mean saturation level of the CCD elements of the CCD camera 18 to optimize signal-to-noise performance. The set point command signal is therefore related to the type of camera employed as well as the web sensitivity. It is desirable to keep the intensity of the stripe of illumination transmitted through the normal coated web 14 (i.e. webs without imperfections) within a narrow range to maintain the camera at the defined fraction of the saturation level regardless of the coating or base optical density which may vary with film or media type. The feedback signal is therefore employed by the illumination controller to maintain the illumination intensity at the camera plane at 80% of the saturation level.

Moreover, it is desirable to maintain the illumination along the stripe on the web 14 uniform and to avoid any falling off or peaks in the intensity profile as viewed at the camera imaging plane. In this regard, intensity uniformity is related primarily to intensity flatness across the length of the linear light beam, and to anomalies, e.g. vignetting or $\cos^4-\theta$ fall-off at the periphery of the camera's field of view (FOV in FIG. 1). Compensation for these anomalies may be implemented with processing algorithms, but at the expense of gray level dynamic range.

Figure 5:
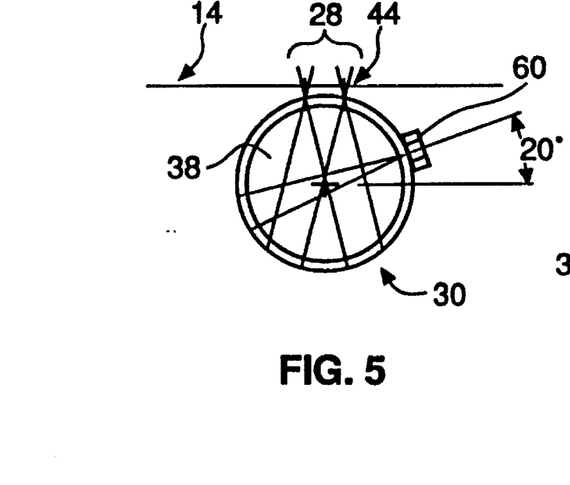
FIG. 5 is an interior end section view taken along lines 4—4 of FIG. 4 in relation to a moving film web illustrating the reflection and scattering of the infrared light emitted by the LEDs within the light integrating cavity and the emission of the integrated light from the exit slit of the housing.
Figure 6:
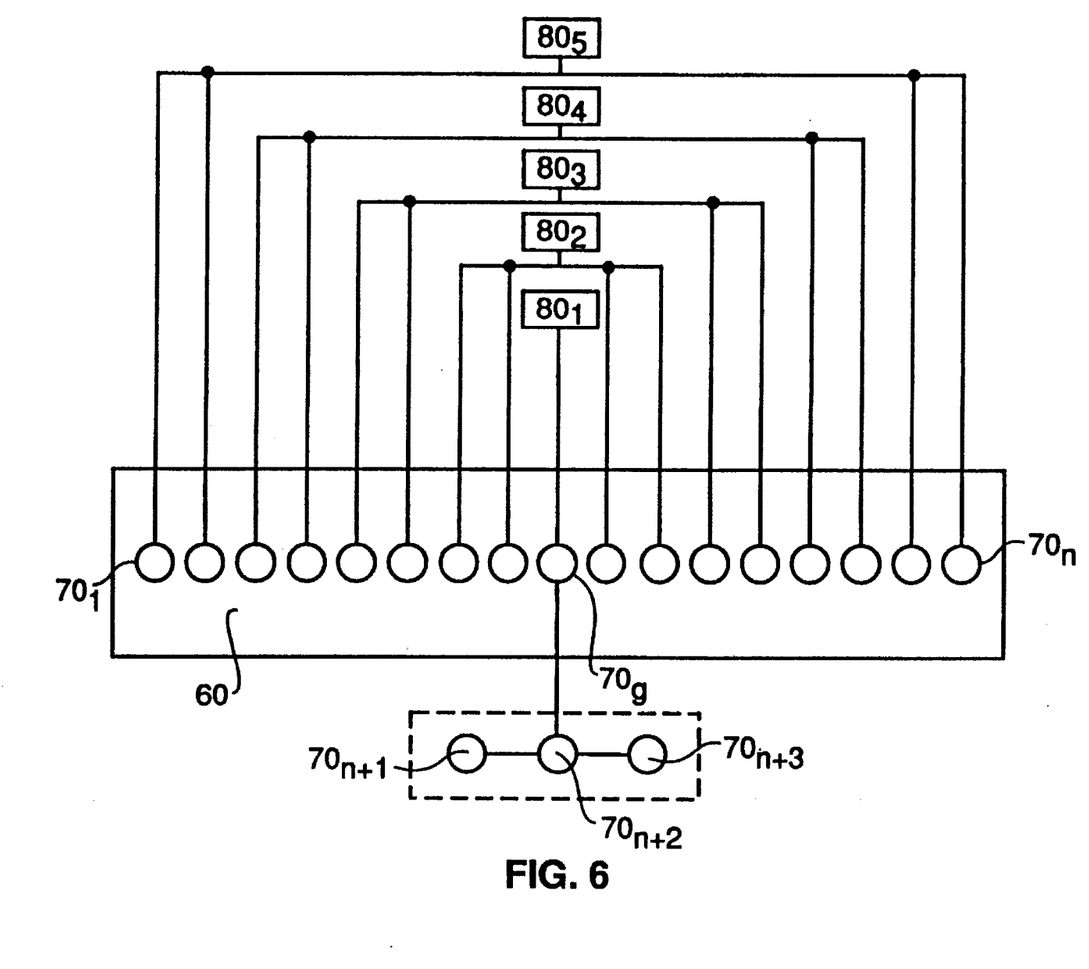
FIG. 6 is a schematic illustration of one embodiment of the clustering of the individual sets of LEDs connected with m respective drive circuits.
Figure 7:
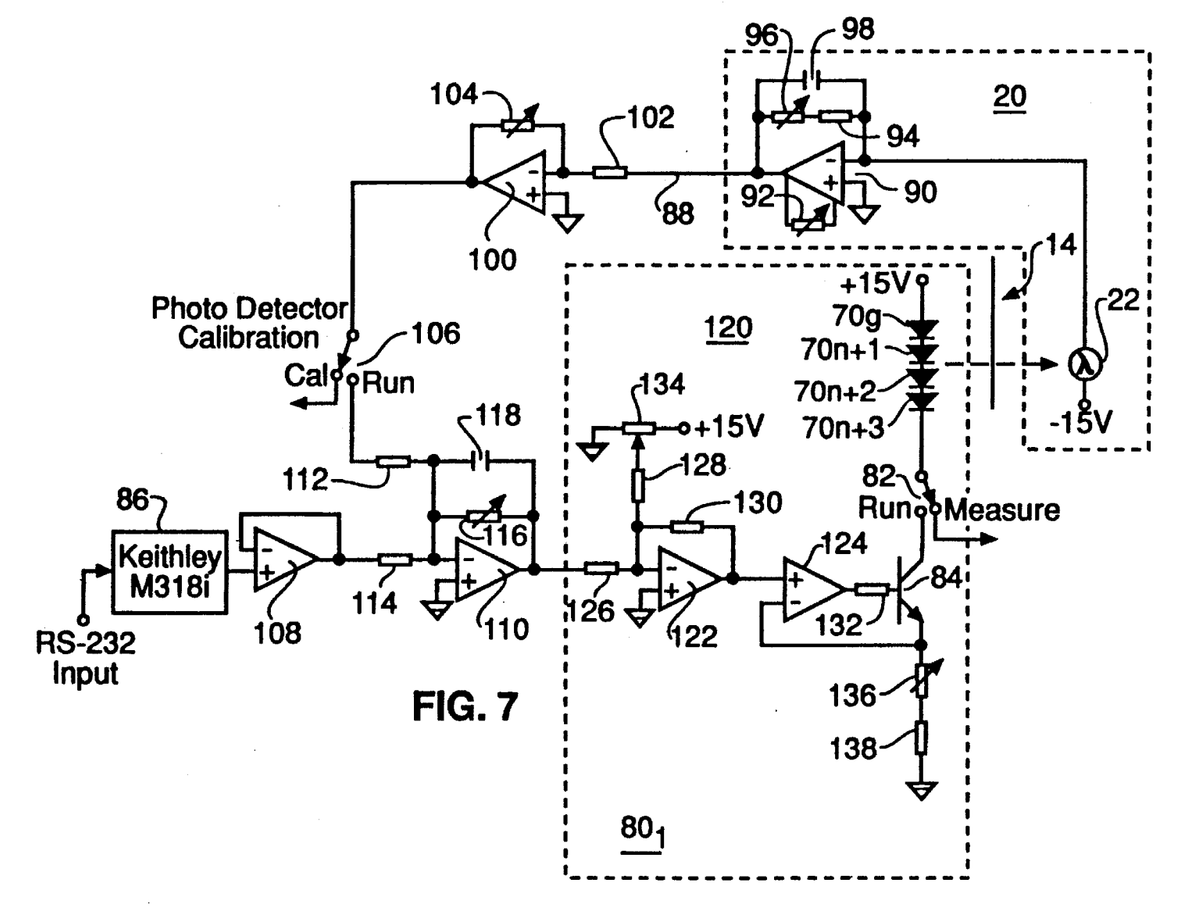
FIG. 7 is a schematic diagram of the adaptive light control drive circuits of FIG. 6

In accordance with the present invention, uniform intensity profile characteristics are realized in a light source 12 formed of a cylindrical light integrator 28 driven by an array of discrete infrared light emitting LEDs and the illumination controller 16 as shown in FIGS. 6 and 7 and described below. Turning now to the mechanical configuration of the light source 12 illustrated in FIGS. 2–5, the light integrator 30 is constructed of an elongated, tubular side wall 32 extending between end walls 34 and 36. The housing may be formed of cast aluminum side wall 32 and end wall 34, 36 caps inserted into the open ends of side wall 32 and screwed into place. The interior surfaces thereof may first be painted in the manner identified in the above-referenced '383 patent., e.g. with "Spectraflect" paint, which is a highly diffusively reflective white paint obtainable from the Labsphere Corp., North Sutton, N.H. The housing parts may alternatively be machined from a plastic material, e.g. "Spectralon" plastic, also available from Labsphere, Corp. or other suitable plastic or metal of the type described in the above-identified '383 patent, where it is not necessary to paint the interior side wall and end surfaces with reflective white paint. In either case, the side wall 32 and end wall 34, 36 caps may be assembled to create the cylindrical light integrating cavity 38 within the walls. A narrow light exiting slit 44 extends lengthwise in the tubular side wall 32 a slit length somewhat shorter than the overall length of the side wall 32. Generally, the slit 44 is long enough to illuminate a linear stripe extending along the width of the moving coated web 14 that is in part imaged in the horizontal FOV direction by the CCD camera 18 imaging array. In a preferred example, employing the above-referenced CCD camera 18 and optical system, the tubular side wall 32 is 9.0 inches (24.5 cm) long and 2.0 inches (5 cm) in outside diameter, and the exit slit 44 is 8.0 inches (20.3 cm) long and 0.5 inches (1.3 cm) wide. The FOV of the camera 18 is 6.0 inches (15.2 cm) long. The side wall 32 is one-sixteenth inch thick, and the end wall caps 34, 36 are one-quarter inch thick. The CCD camera 18 therefore images a 6.0 inch (15.2 cm) long, 2048 pixel, line scan of the 8.0 inch (20.3 cm) long by 0.5 inch (1.3 cm) wide illuminated stripe of the web 14.

Figure 4:
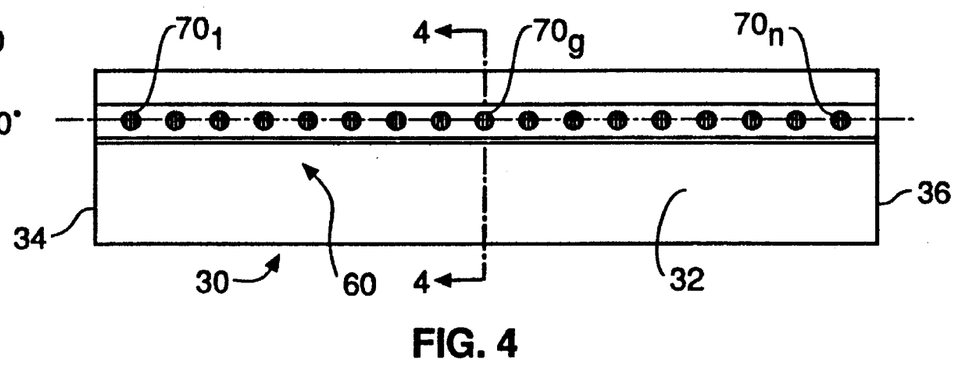
FIG. 4 is a exterior plan view of the linear light integrator housing with detail illustrating the placement of n infra-red LEDs to emit infra-red light into the light integrating cavity.

An LED element array 60 is formed of a support bar 62 supporting n LEDs $70_1$–$70_n$ facing into the light integrating cavity 44. The LEDs $70_1$–$70_n$ are evenly spaced apart from one another along the length of the support bar 62 on 0.5 inch (1.3 cm) centers in the preferred example. The support bar 62 is attached to the side wall 32 of the light integrator 28, so that the n LEDs $70_1$–$70_n$ face into a light admitting slit or individual holes for each LED $70_i$ in the side wall 32. The center most LED $70_9$ is centered on the center point 46 of slit 44.

As shown in FIG. 4, the n=17 GaAlAs infrared radiation emitting LEDs $70_i$ are arranged in a linear array distributed evenly along the axial direction of the light integrator 28. Each LED $70_i$ produces approximately 12 mW of power when operated at 100 mA, the maximum allowable continuous current. The peak emitted wavelength is near 880 nm.

The positioning of the LED array 60 is at an angle of 70° to the exit slit 44, in the example depicted. Most of the infra-red light emitted by the LEDs $70_1$–$70_n$ reflects two or more times from the diffusively reflecting white inner surfaces of the light integrating cavity 38 before exiting the slit 44 as depicted in FIG. 5. The illuminated stripe 28 of the web 14 as viewed from the CCD camera 18 is also shown in FIG. 5. The camera is positioned so that the illumination reflected from the interior side wall of the integrating cavity directly opposite to the exit slit 44 does not include light directly emitted by the LEDs or reflected only once from the interior side wall surface of the integrating cavity.

The equal distribution of the LEDs $70_1$–$70_n$ along the support bar 62 gives rise to intensity variation in the linear light beam emitted from the slit 44. Due to the optically related anomalies, as well as intensity roll off at the cavity end points, and possible LED non-uniformities, the illumination profile of linear light beam, as imaged on the CCD array of camera 18 falls off at both ends of the FOV. The compensation for these combined effects is accomplished with dedicated offset adjustments for each set of LED cluster drivers, described below, to cause the light intensities emitted by m groups of the n LEDs $70_1$–$70_n$ to be preset in a manner that compensate and render the light intensity profile more uniform.

In this regard, in order to make the illumination intensity more even and the intensity profile flatter, the n LEDs $70_1$–$70_n$ (and an additional set of "dummy" LEDs $70_{n+1}$, $70_{n+2}$ and $70_{n+3}$) are clustered into m groups in accordance with the present invention. The emitted light intensity of each group may be individually adjusted in response to a separate adjustment voltage to even out the intensity of the light emitted from the slit 44 as viewed at the camera imaging focal plane. In other words, the intensity of light emitted by each group may differ, yet the integration of the light in the linear light integrator 30 causes the intensity profile of the emitted light beam to be more uniform in the illuminated stripe 28 as viewed at the imaging plane of the CCD camera 18.

FIG. 6 is a schematic illustration of one embodiment of the clustering of the n individual LEDs $70_1$–$70_n$ into m groups of an equal number n/m LEDs connected with m respective drive circuits of the type shown in FIG. 7 in order to tailor the intensity profile along the length of the slit 44. In the example illustrated, n=17 equally spaced apart and extending away from the center most LED $70_9$ along the nine inch long support bar 62. The LEDs $70_1$–$70_8$ and $70_{10}$–$70_{17}$ are clustered into four group LEDs each on either side of the center most LED $70_9$. The three additional "dummy" LEDs $70_{n+1}$, $70_{n+2}$ and $70_{n+3}$ are hidden inside the electronics chassis and are clustered with the center most LED $70_9$ to ensure equivalent transfer characteristics for all diode clusters. As a result, the total number of groups m =5, and the number of LEDs 70 in each group are equal at n/m =4.

The particular number n of active LEDs employed depends on the length of the FOV chosen and a variety of other hectors. Generally, given the length of the integrating cavity 12 needed for the scanning application, the selection of the number n of LEDs and spacing may be derived using standard ray tracing techniques. The smallest number of LEDs is desired that will provide a reasonable range of intensity adjustment capability to accommodate the variations in intensity needed to illuminate differing web types.

Similarly, the number of groups m may be varied. Symmetry in the selection of LED groups about the center of the cavity may not be necessary or desirable in the given application. And, certain of the clusters may have differing numbers of LEDs than others. In the extreme case, each LED might form its own group and be driven separately to a separate intensity level.

Each of the clusters of FIG. 6 is electrically driven by one of the five adaptive light control drive circuits $80_1$–$80_5$, typified by the center most LED drive circuit $80_1$ schematically illustrated in FIG. 7 together with the common components of the illumination controller 16 and the feedback photodetector 20. In FIG. 7, the LEDs $70_{n+1}$, $70_{n+2}$ $70_{n+3}$, and $70_9$ are connected electrically in series through a current bypass switch 82 as an LED cluster load to drive transistor 84. Energizing the drive transistor 84 causes current to flow through the cluster of LEDs, and the LEDs emit infra-red light of an intensity dependent on the applied current level. To implement remote illumination level control, a Keithley M3181 module 86 converts the serial RS-232 code set point generated by the work station 40 to a 0 to 10 volt analog set point level signal.

As described above in reference to FIG. 1, the average intensity of the stripe of infra-red light transmitted through the sensitized film web 14 varies as a function of the emulsion coatings and film base type densities. It is desired, in accordance with a further aspect of the invention, to maintain the intensity of the light transmitted through the web 14 and reaching the CCD camera 18 within a certain intensity range to accommodate the optimum signal-to-noise operating characteristics of the CCD elements and to be able to discriminate streaks in the coated film layers from normal film layers. The drive circuits $80_1$–$80_5$ are coupled to a common feedback network for continuously adjusting the drive current to each drive transistor 84 as a function of the feedback signal level, dependent on the average transmissivity characteristics of the sensitized film web 14, and the value of the set point signal. The computer generated set point is established during the set-up in relation to the 80% saturation level of the camera being used and is applied by the work station 40 to the illumination controller 16.

The feedback network includes the photo diode 22 of the feedback photodetector 20 arranged alongside the CCD camera 18 of FIG. 1 for providing a feedback signal related to the intensity of the infra-red light radiation transmitted through coating layers of the specific type of coated web 14. Changes in the average LED radiation intensity, as viewed through the coated web 14 by the discrete photo diode 22 are conditioned for comparison with the computer generated set point. The resultant error signal is amplified to modulate the drive currents provided by the LED driver circuits so as to cause corrective action in the illumination level. The net effect is to maintain the specified fixed illumination operating level as seen by the CCD camera 18, regardless of coating density variations.

Turning to FIG. 7, the photodetector 20 includes an integrated photo diode 22 and a current-to-voltage preamplifier 90. The operating state for pre-amplifier 90 is adjusted by appropriate values for the variable resistor 96, the resistor 94, the capacitor 98 and a variable offset resistor 92. The pre-amplifier output signal is also conditioned by the amplifier 100, the operating state of which is adjusted by appropriate selection of values for the resistor 102 and variable resistor 104 to provide the amplified signal to a calibration switch 106. The calibration switch 106 is normally in the Run position during operation of the drive circuit $80_i$, but may be moved to the Calibration position in order to facilitate LED current driver set-up during calibration procedures. In the Calibration position of switch 106, the feedback is cut out, and the output signal rises to 100%. With current bypass switch 82 set to the Measure position, an ammeter is introduced in series with the series connected LED set to measure current drawn during calibration. The resistors are adjusted to a level that ensures that the rated current through the LEDs is not exceeded.

The conditioned negative feedback signal is compared at the feedback amplifier 110 summing junction with the set point signal, from inverter 108, which is driven by the Keithley serial-to-analog module 86. The feedback amplifier 110 is also an operational amplifier connected at one input as shown to the summing resistors 112, 114 and to the variable resistor 116 and capacitor 118 to provide a signal at its output representative of the difference between the set point signal level and the feedback signal level. The amplified error signal is applied in common to each of the adaptive light control drive circuits $80_1$–$80_5$ of FIG. 6.

In each adaptive light control drive circuit, the amplified error signal from feedback amplifier 110 is input to the LED module driver 120 consisting of amplifier 122, and the associated fixed resistors 126, 128, 130, and variable resistor 134, and amplifier 124, and associated variable resistor 136 and fixed resistor 138. Amplifier 122 provides additional voltage gain as well as a cut-off limit to the voltage input to amplifier 124.

Drive transistor 84 and amplifier 124 are configured as a linear voltage-to-current device for powering and controlling the intensity of the series-connected LED cluster. The voltage across resistors 136 and 138 is forced to track the voltage at the input of amplifier 122. The transistor 84 collector-emitter current through the series-connected LED cluster (in this case LEDs $70_9$, $70_{n+1}$, $70_{n+2}$, $70_{n+3}$) and resistors 136 and 138 allows a linear response to the input signal level.

The variable resistor 134 is adjusted across a 15 volt supply that enables a selectable fixed voltage level to be connected to amplifier 122 through input resistor 128. Each variable resistor 134 of each of the adaptive light control drive circuits $80_1$–$80_5$ is adjusted separately during set up of the light integrator 30, but could, if necessary, be adjusted to account for aging of the light sources, or the like. The adjustment is made while measuring the light output across the light stripe as viewed from the camera imaging plane. Each of the resistor 126, 128, and 130 values are also selected to limit the maximum voltage to the input of amplifier 124 (to in turn limit current driven through the series connected LEDs) in the event amplifier 110 is turned full on.

The average operating level of each LED cluster is thereby independently tailored with respect to creating a desired net compensation profile at light exiting slit 44 leading to a more uniform intensity across the illuminated stripe 28 as viewed at the camera imaging plane in accordance with the invention.

Experimental Procedures and Results

Figure 8:
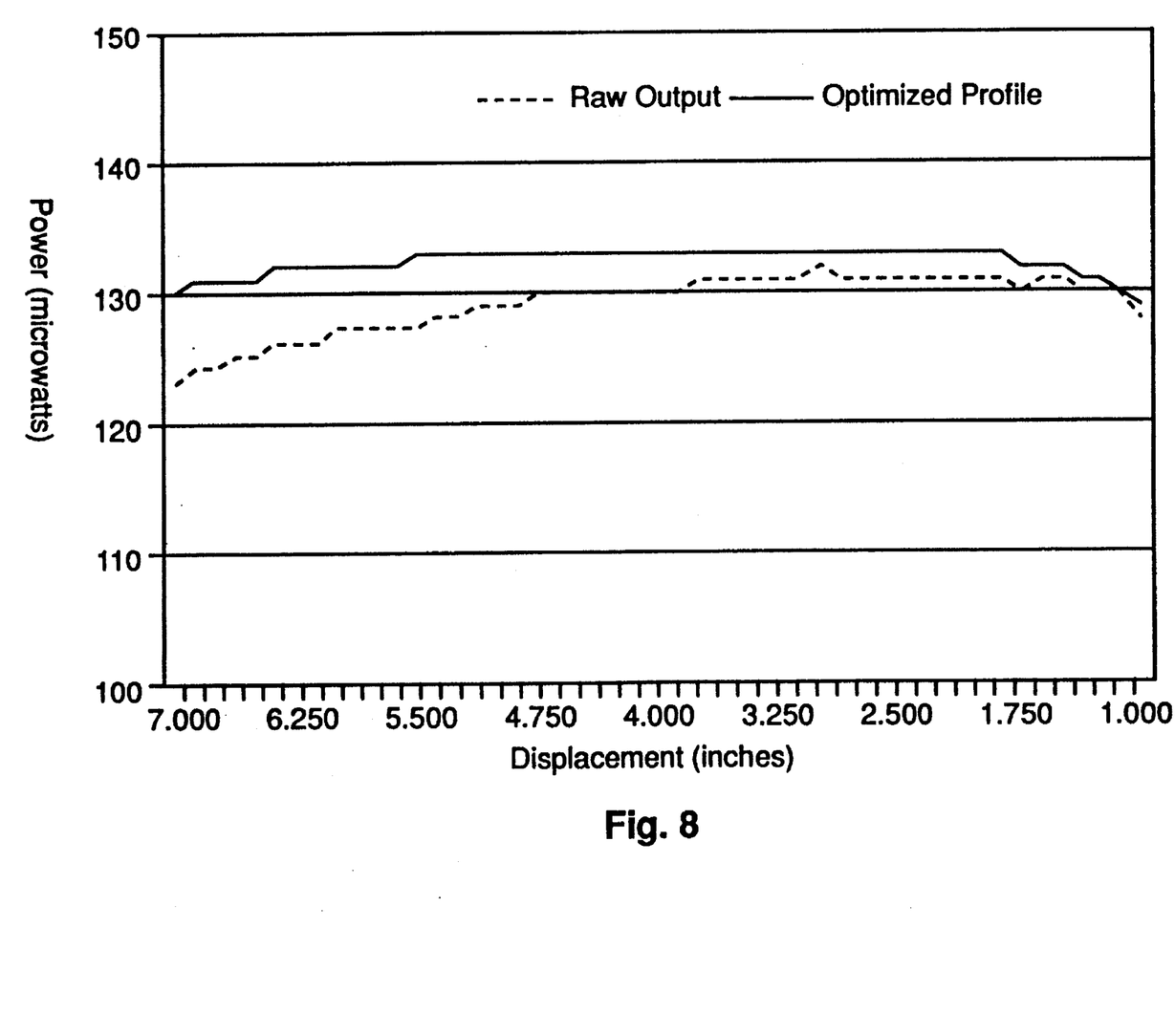
FIG. 8 is a graph comparing uncompensated with optimized illumination intensity profiles vs. spatial displacement achieved by appropriate adjustment of the LED drive circuits in accordance with an embodiment of the invention.

FIG. 8 is a graph illustrating the uncompensated and optimized illumination intensities of radiation emitted vs. displacement of slit 44 achieved by adjustment of the adaptive light control drive circuit resistors 134. A fixture was fabricated to enable transit of a radiometer head across the center 6.0 inches (15.2 cm) of the integrating cavity output slit 44. Initial measurements were taken at ⅛ inch increments at a distance ½ inch from the aperture opening, with all LEDs 70 driven at 100 mA to derive the uncompensated intensity profile depicted in dashed lines. The individual LED cluster drivers 80 were then adjusted so as to optimize the uniformity of the measured intensity profile, and the measurements for this condition were recorded. The resulting optimized or compensated profile is plotted in FIG. 8 as the solid line.

Figure 9:
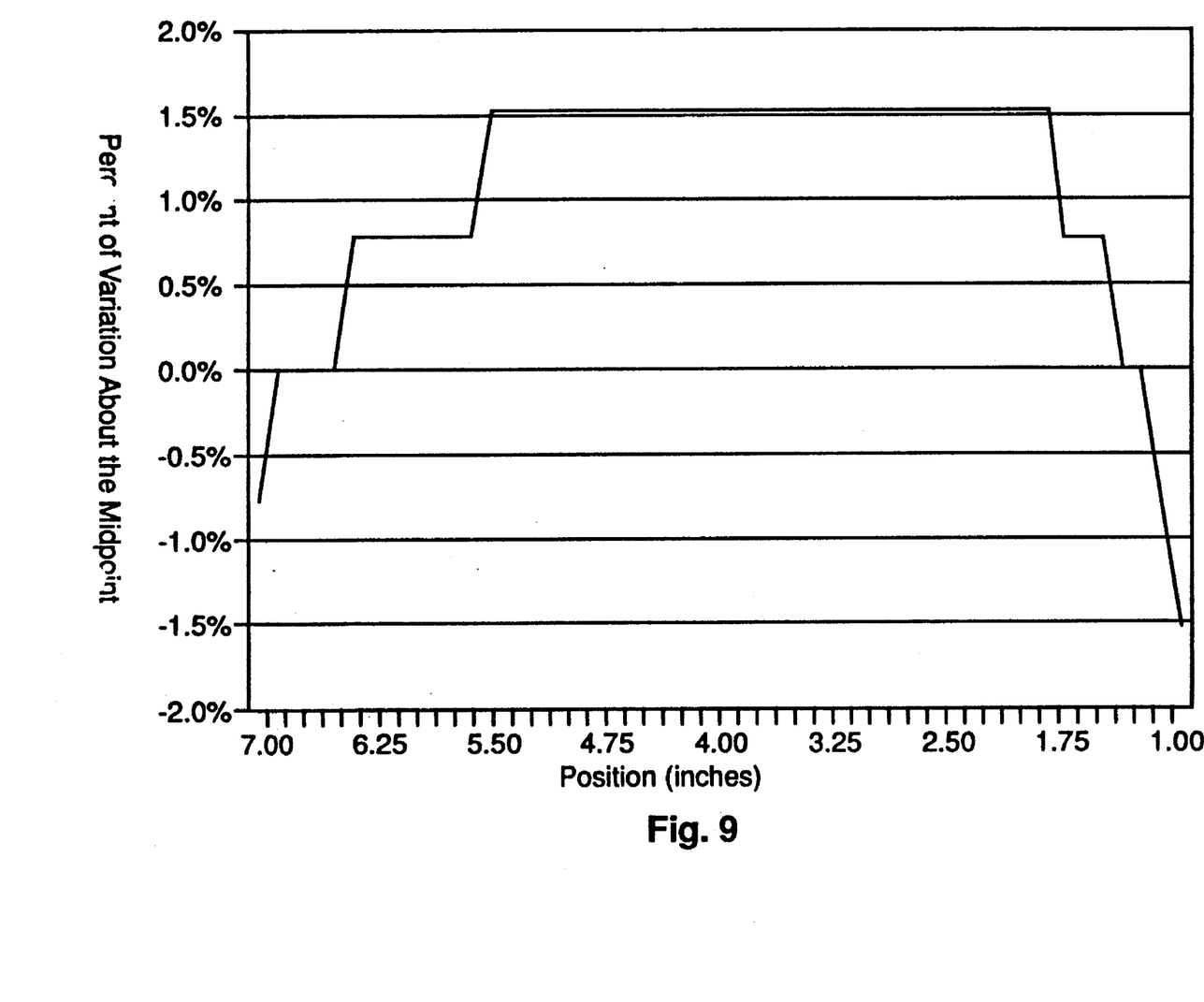
FIG. 9 is a graph showing the percentage of deviation from the intensity profile midpoint level vs. spatial displacement for the optimized case.

For the case of the optimized intensity profile, the relative deviation from the gray level mid point was calculated for each data point, and the results are plotted in FIG. 9. The expected intensity fall-off occurs within 2.0 to 2.5 inches (5.0–6.2 cm) from either end of the 8.0 inch (20.3 cm) long output aperture of the integrating cavity 12. The worst case deviation of the intensity profile midpoint at any measured position along the aperture is on the order of plus or minus 1.5 percent.

Data for the transfer function for illumination levels vs. light control set point was acquired using the CCD camera. The camera was equipped with a 35 mm camera lens with a focal length of 35 mm, and the aperture was set to f/4.0. The front of the lens was located at an approximate distance of 17.0 inches (43 cm) from the slit 44. A graded neutral density filter was positioned 0.5 inches (1.3 cm) from the slit 44. The frame grabber 24 was used to format line output into 512 by 2048 pixel frames. From this synthesized frame data, gray level histogram statistics were derived as a pragmatic means of determining the intensity response to a range of set point inputs.

Figure 10:
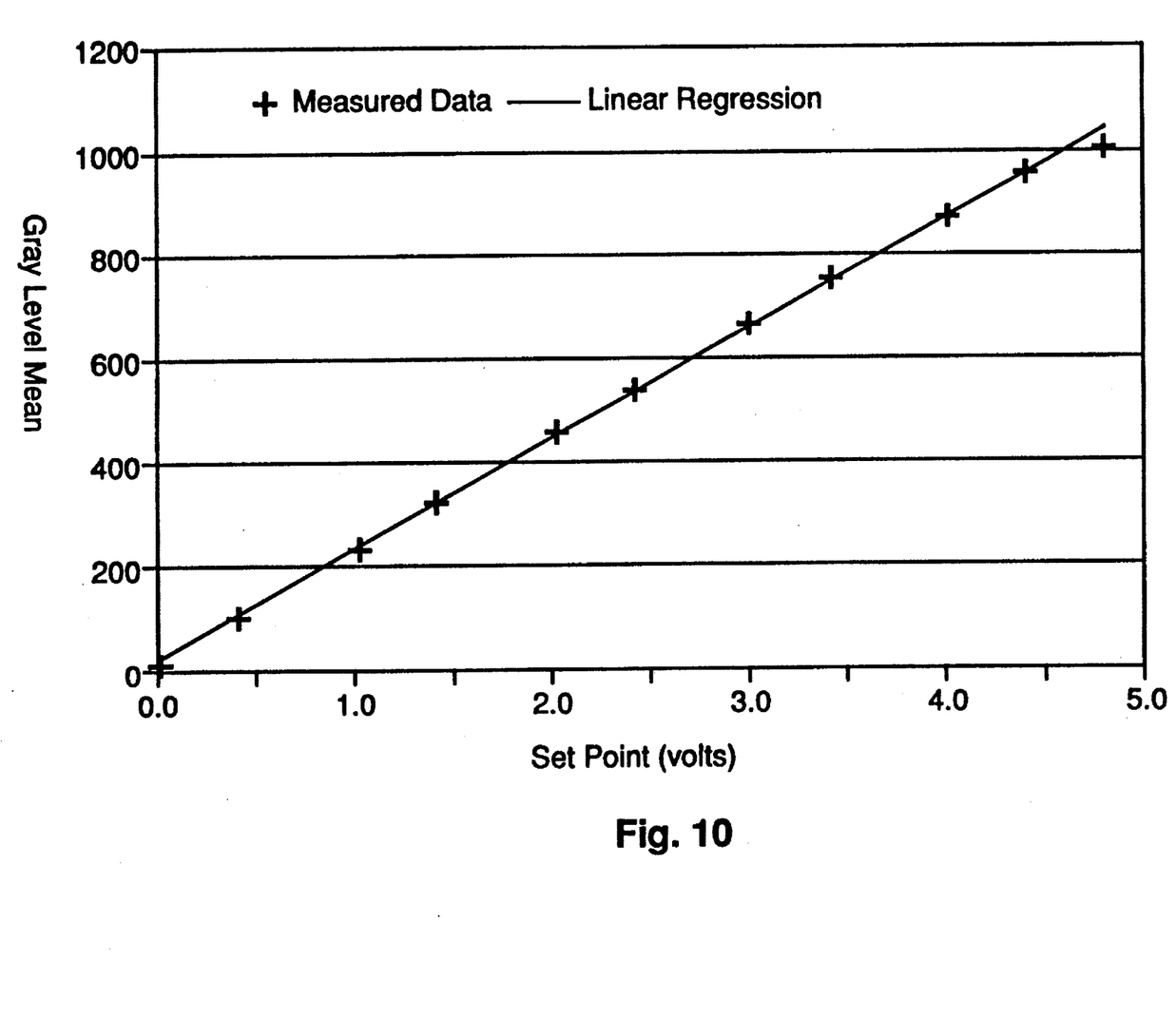
FIG. 10 is a graph illustrating the linearity of the gray level mean output as measured at the camera vs. the set point input at the LED controller circuit.

Graded neutral density filters were inserted between the illumination source, and the camera. With the set point value adjusted to generate an 80% CCD saturation level, camera output was observed for a range of 0 to 2.0 optical density units. The illumination measurements remained constant for the full range of density values. For the case of a 2.0nd filter, set point input for the controller was varied from 0 to 10 volts. For each input value, the associated gray level image histogram mean was recorded. The linearity of the relationship between illumination output rs. set point is documented in FIG. 10.

Given the quality of illumination uniformity through the center region of the slit 44, it is reasonable to expect that extrapolations of this design would provide the same quality of uniformity for wider coated web applications. For wide webs, it may be prudent to extend the integrating cavity to a length that exceeds the width of the web at each end so that the slit 44 extends beyond the edges of the web to avoid the light intensity fall off at the ends of the linear light beam.

For some sensitized product applications, it is desirable to have the capability to vary illumination wavelength. The present invention may be implemented by installing separate wavelength LED anay strips to emit selected wavelengths of light within a single integrating cavity.

Moreover, although the linear light integrator described in the description of the preferred embodiment employs uniformly spaced LEDs grouped into symmetric clusters about the center-most LED, it will be understood that the invention embraces other spacings and groupings that may be found appropriate to provide the desired light intensity profile. The LED clusters may also vary in number of LEDs in each cluster as warranted to achieve the desired intensity uniformity profile. Although a more uniform intensity profile as viewed from the imaging camera is achieved in the preferred embodiment, other intensity profiles across the length of the linear light beam may be tailored by the spacing and grouping of the LED clusters and/or by adjusting the light intensity emitted by each LED cluster.

Although several embodiments of the present invention have been illustrated in the accompanying drawings and described in the foregoing detailed description, it will be understood that the invention is not limited to the particular embodiments described herein, but is capable of numerous rearrangements, modification and substitutions without departing from the scope of the invention. The following claims are intended to encompass all such modifications.

PARTS LIST FOR FIGS. 1–10

10 ......... coating density analyzer
12 ......... linear light source
14 ......... sensitized film web
16 ......... illumination controller
18 ......... CCD camera
20 ......... feedback photodetector
22 ......... photo diode
24 ......... frame grabber
26 ......... image storage
30 ......... linear light integrator
32 ......... tubular side wall
34 and 36 ....... end walls
38 ......... light integrating cavity
40 ......... work station
42 ......... monitor
44 ........ light exiting slit
46 ........ center point
60 ........ LED element array
62 ........ support bar
$70_1$–$70_n$ ........ n LEDs
$80_i$, $80_1$–$80_5$...... adaptive light control drive circuits
82 ......... current bypass switch
84 ......... drive transistor
86 ......... module
88 ......... line
90 ......... operational amplifier
92 ......... variable offset resistor
94 and 96 ....... fixed and variable gain resistors
98 ......... capacitor
100 ....... second amplifier
102 ....... fixed resistor
104 ....... variable resistor
106 ....... calibration switch
108 ....... inverter
110 ....... summing amplifier
112, 114 ......... summing resistors
116 ....... variable resistor
118 ....... capacitor
120 ....... LED driver amplifier
122, 124 ......... operational amplifiers
126, 128, 130, 132 ........ fixed resistors
134 ....... variable resistor
136 ....... variable resistor
138 ....... fixed resistor

We claim:

1. A linear light integrator for use in illuminating a web with an elongated stripe of diffuse illumination comprising:

an elongated housing formed with side and end walls defining a light integrating cavity having diffusely reflecting interior wall surfaces, said housing side wall having a longitudinally extending slit through which diffuse light exits said cavity;

an elongated array comprising a plurality of discrete light sources supported with respect to the elongated housing to emit light into said cavity, whereby the emitted light is integrated within the cavity by reflection from the interior wall surfaces thereof and the integrated light forms a linear light beam exiting the elongated slit having a varying longitudinal intensity profile; and means for modulating the intensity of the light emitted by said discrete light sources in a predetermined intensity pattern for altering the varying longitudinal intensity profile of the linear light beam to provide a desired longitudinal intensity profile of the stripe of diffuse illumination, said intensity modulating means further comprises:

means for providing a set point control signal defining an illumination intensity level of said stripe of illumination;

means for connecting said plurality of light sources into a further plurality of groups in a predetermined relationship; and a plurality of drive circuits for driving each of said plurality of groups of light sources at a plurality of light intensities corresponding to said predetermined intensity pattern as a function of said set point control signal for altering the varying longitudinal intensity profile of the linear light beam to provide the desired longitudinal intensity profile of the stripe of diffuse illumination.

2. The linear light integrator of claim 1 further comprising:

means for monitoring the intensity of the linear light beam modulated by the web and providing an intensity feedback signal varying as a function of the light transmissive characteristics of the web;

means for comparing said set point control signal with said intensity feedback signal and deriving an error signal from the comparison; and wherein said plurality of drive circuits further comprises:
means for providing drive energy to said plurality of light sources in each group to establish the plurality of light intensities of the groups of light sources; and means responsive to the error signal for adjusting the drive energy provided to maintain the plurality of light intensities in a constant relationship regardless of the light transmissive characteristic of the web.

3. The linear light integrator of claim 2 wherein said plurality of light sources are equally spaced and are supported in a linear light source array aligned in parallel with said longitudinally extending light exiting slit.

4. The linear light integrator of claim 3 wherein:
said plurality of light sources are equidistantly spaced in said light source array with an array center point of said light source array being aligned with a slit center point of said longitudinally extending light exiting slit; and said connecting means makes electrical connections of groups of said light sources selected from said light source array on either side of said array center point.

5. The linear light integrator of claim 4 wherein:
certain of said groups comprise an equal number of light sources selected from said light source array on either side of said array center point to effect a symmetric level of illumination along said light source array with respect to said array center point.

6. The linear light integrator of claim 5 wherein:
said light source array is supported to emit light into said cavity from said cavity side wall at an angular displacement of greater than 0° and less than about 90° with respect to said elongated slit, so that the light emitted into said cavity is not directed directly into said slit or against the side wall interior surface directly opposite to the slit and the reflection is not directly visible through said light exiting slit from a predetermined position.

7. The linear light integrator of claim 6 wherein said angular displacement is at about 70°.

8. The linear light integrator of claim 5 wherein:
a single light source having a single source load is positioned at said array center point, and the remaining light sources are arranged in equal numbers extending in said light source array away from the center most single light source;

said certain groups each comprise a further equal number of light sources selected from said remaining light sources on either side of said center most single light source to effect a symmetric connection of the light sources in each group about said center most light source and a symmetric pattern of illumination intensity along said light source array with respect to said array center point, said equal number of light sources connected in each group presenting a substantially equal electrical group load; and further comprising:

means coupled to said single light source for augmenting the single light source load to equal that of said group load.

9. The linear light integrator of claim 1 wherein:
said plurality of light sources being equally spaced is supported in a linear light source array aligned in parallel with said longitudinally extending light exiting slit to emit light into said cavity from said cavity side wall at an angular displacement of greater than 0° and less than about 90° with respect to said elongated slit, so that the light emitted into said cavity is not directed directly into said slit or against the side wall interior surface directly opposite to the slit and the reflection is not directly visible through said light exiting slit from a predetermined position.

10. The linear light integrator of claim 9 wherein said angular displacement is at about 70°.

11. The linear light integrator of any of the claims 1 through 10 wherein said web is a sensitized film and said plurality of light sources comprise infrared LEDs of a wavelength chosen to avoid fogging of said sensitized film.

12. A scanner for scanning an illuminated stripe of a moving web for detecting defects in the web comprising:
a linear light integrator for use in illuminating said web with a stripe of diffuse illumination at a web scanning plane further comprising:
an elongated housing formed with side and end walls defining a light integrating cavity having diffusely reflecting interior wall surfaces, said housing side wall having a longitudinally extending slit through which diffuse light exits said cavity; and an elongated array of a plurality of discrete light sources supported with respect to the elongated housing for emitting light into said cavity, whereby the emitted light is integrated within the cavity by reflection from the interior wall surfaces thereof and the integrated light forms a linear light beam exiting the elongated slit having a varying longitudinal intensity profile;

a line imaging camera imaged on an image scan line of said illuminated stripe of said web for developing an output image signal varying in magnitude as a function of the transmission of light through areas of said web that exhibit normal and defective densities; and means for modulating the intensity of the light emitted by said discrete light sources in an intensity pattern to provide a desired longitudinal intensity profile of said stripe of diffuse illumination illuminating the web as viewed by said line imaging camera, said intensity modulating means further comprises:
means for providing a set point control signal defining an illumination intensity level of said stripe of illumination for the imaging camera being used;
means for connecting said plurality of light sources into a further plurality of groups in a predetermined relationship;
a plurality of drive circuits for driving each of said plurality of groups of light sources at a plurality of light intensities corresponding to said predetermined intensity pattern as a function of said set point control signal for altering the varying longitudinal intensity profile of the linear light beam to provide the desired longitudinal intensity profile of said stripe of diffuse illumination.

13. The scanner of claim 12 further comprising:
means for monitoring the intensity of the linear light beam modulated by the web and providing an intensity feedback signal varying as a function of the light transmissive characteristics of the web;

means for comparing said set point control signal with said intensity feedback signal and deriving an error signal from the comparison; and wherein said plurality of drive circuits further comprises:
  means for providing drive energy to said plurality of light sources in each group to establish the plurality of light intensities of each group of light sources; and
  means responsive to the error signal for adjusting the drive energy provided to maintain the plurality of light intensities in a relative intensity pattern relationship regardless of the light transmissive characteristic of the web.

14. The scanner of claim 12 further comprising:
means for monitoring the intensity of the linear light beam modulated by the web and providing an intensity feedback signal representative thereof to each of said plurality of drive circuits, said intensity feedback signal waiting as a function of a characteristic of the web; and
wherein said plurality of drive circuits further comprise:
  means for providing drive energy to said plurality of light sources in each group to establish the plurality of light intensities of the groups of light sources; and
  means responsive to the intensity feedback signal for adjusting the drive energy provided to maintain the plurality of light intensities in a relative intensity pattern relationship.

15. The scanner of claim 14 wherein said plurality of light sources are equally spaced and are supported in a linear light source array aligned in parallel with said longitudinally extending light exiting slit.

16. The scanner of claim 15 wherein:
said plurality of light sources are equidistantly spaced in said light source array with an array center point of said light source array being aligned with a slit center point of said longitudinally extending light exiting slit; and
said connecting means makes electrical connections of groups of said light sources selected from said light source array on either side of said array center point.

17. The scanner of claim 16 wherein:
certain of said groups comprise an equal number of light sources selected from said light source array on either side of said array center point to effect a symmetric level of illumination along said light source array with respect to said array center point.

18. The scanner of claim 17 wherein:
said light source array is supported to emit light into said cavity from said cavity side wall at an angular displacement of greater than 0° and less than about 90° with respect to said elongated slit, so that the light emitted into said cavity is not directed directly into said slit or against the side wall interior surface directly opposite to the slit and the reflection is not directly visible through said light exiting slit from said line imaging camera.

19. The scanner of claim 18 wherein said angular displacement is at about 70°.

20. The scanner of claim 17 wherein:
a single light source is positioned at said array center point, and the remaining light sources are arranged in equal numbers extending in said light source array away from the center most single light source;
said certain groups each comprise a further equal number of light sources selected from said remaining light sources on either side of said center most single light source to effect a symmetric connection of the light sources in each group about said center most light source and a symmetric pattern of illumination intensity along said light source array with respect to said array center point, said equal number of light sources connected in each group presenting a substantially equal electrical group load; and further comprising:
means coupled to said single light source for augmenting the single light source electrical load to that of said group load.

21. The scanner of claim 12 wherein:
said plurality of light sources being equally spaced is supported in a linear light source array aligned in parallel with said longitudinally extending light exiting slit to emit light into said cavity from said cavity side wall at an angular displacement of greater than 0° and less than about 90° with respect to said elongated slit, so that the light emitted into said cavity is not directed directly into said slit or against the side wall interior surface directly opposite to the slit and the reflection is not directly visible through said light exiting slit from said line imaging camera.

22. The scanner of claim 21 wherein said angular displacement is at about 70°.

23. The scanner of any of the claims 13 through 22 wherein said web is a sensitized film and said plurality of light sources comprise infrared LEDs of a wavelength chosen to avoid fogging of said sensitized film.

* * * * *